(12) United States Patent
Wallace et al.

(10) Patent No.: US 8,919,349 B1
(45) Date of Patent: Dec. 30, 2014

(54) FOOT EXFOLIATION DEVICE

(76) Inventors: Gary L. Wallace, Morgantown, KY (US); Cathy Wallace, Morgantown, KY (US)

(*) Notice: Subject to any disclaimer, the term of this patent is extended or adjusted under 35 U.S.C. 154(b) by 340 days.

(21) Appl. No.: 13/555,622

(22) Filed: Jul. 23, 2012

(51) Int. Cl.
*A45D 29/18* (2006.01)

(52) U.S. Cl.
USPC .......................................... 132/76.5; 451/533

(58) Field of Classification Search
CPC  A45D 29/18; A45D 29/20; A45D 2200/1054
USPC ............ 132/73, 76.2, 76.5, 76.4; D28/59, 56; 451/533, 538, 539; 606/131
See application file for complete search history.

(56) References Cited

U.S. PATENT DOCUMENTS

| | | | | |
|---|---|---|---|---|
| 1,896,253 A | * | 2/1933 | Smith | 451/530 |
| 3,870,058 A | * | 3/1975 | Merriman | 132/73 |
| 4,437,271 A | * | 3/1984 | McAvoy | 451/532 |
| 4,930,529 A | * | 6/1990 | Whitney | 132/73 |
| 5,671,498 A | | 9/1997 | Martin et al. | |
| 6,290,707 B1 | | 9/2001 | Street | |
| D474,610 S | | 5/2003 | Park et al. | |
| 6,991,527 B2 | * | 1/2006 | Linzell | 451/523 |
| 7,264,542 B1 | * | 9/2007 | Leyva | 451/494 |
| D578,718 S | | 10/2008 | Bettanin | |
| 2010/0037906 A1 | * | 2/2010 | Ionis et al. | 132/76.5 |

* cited by examiner

*Primary Examiner* — Rachel Steitz
(74) *Attorney, Agent, or Firm* — Crossley Patent Law

(57) ABSTRACT

A foot exfoliation device including a base tray having non-slip surface member disposed on a bottom side thereof; a continuous wall disposed on the base tray top side proximal the periphery thereof; and a trough continuously disposed on the top side inside the wall. Stacked sand paper sheets are disposed within the trough. A removable snap-on cover is disposed atop the base tray. A sand paper post member, which is centrally disposed within the trough proximal to a base tray front end, permits exfoliation between toes. An aperture, centrally disposed proximal to a forward end of each of the sand paper sheets, slidingly receives the post member therethrough. A mirror is disposed on an underside of the cover to permit inspection of the user's feet.

6 Claims, 4 Drawing Sheets

FOOT EXFOLIATION DEVICE

BACKGROUND OF THE INVENTION

Various types of exfoliation devices are known in the prior art. However, what is needed is a portable, lightweight foot exfoliation device that permits exfoliation from a seated position, the device including a base tray having non-slip surface member disposed on the bottom side thereof; a continuous wall disposed on the base tray top side proximal the periphery thereof; and a trough continuously disposed within the base tray inside the wall. Stacked sand paper sheets are disposed within the trough for exfoliating the feet. A removable snap-on cover is disposed atop the base tray. A sand paper post member is centrally disposed within the trough and proximal to a base tray front end. The sand paper post member permits exfoliation between toes. An aperture, centrally disposed proximal to a forward end of each of the sand paper sheets, slidingly receives the post member therethrough. A mirror is disposed on an underside of the cover to permit inspection of the user's feet.

FIELD OF THE INVENTION

The present invention relates to exfoliation devices, and more particularly, to a foot exfoliation device.

SUMMARY OF THE INVENTION

The general purpose of the present foot exfoliation device, described subsequently in greater detail, is to provide a foot exfoliation device which has many novel features that result in a foot exfoliation device which is not anticipated, rendered obvious, suggested, or even implied by prior art, either alone or in combination thereof.

To accomplish this, the present foot exfoliation device is portable and lightweight and allows exfoliation of a user's feet while in a seated position. The present device includes a base tray with a non-slip surface member disposed on a bottom side thereof to prevent the device from moving during use to exfoliate a user's feet. A continuous wall is disposed on a top side of the base tray proximal a periphery thereof. A trough is continuously disposed within the base tray inside the wall and covers substantially the entire top side of the base tray. Sand paper sheets stacked atop each other are disposed within the trough. A snap-on cover is disposed atop the base tray. A sand paper post member is centrally disposed within the trough and proximal to a base tray front end of the base tray. The post member permits exfoliation between toes. An aperture, centrally disposed proximal to a forward end of each of the sand paper sheets, slidingly receives the post member therethrough to secure the sand paper sheets within the trough.

A lip, centrally disposed on at least one of a front side and a rear side of the cover, has a rearward extension member that lockingly engages and alternately disengages a recess centrally disposed on at least one of a respective forward side and a rearward side of the wall to place the cover in a closed position with an outside perimeter of the cover disposed atop a ledge continuously adjacent the wall and alternate open position. Alternately upon the disengagement of the lip rearward extension member from the recess, the cover is placed in an open position. A forward extension member of the lip permits a user to grip the cover for removal from the base tray. An unbreakable mirror, disposed on substantially an entire underside of the cover, permits inspection of the user's feet to determine completion of exfoliation without having to place a user's body in a contorted position to inspect his feet.

To use the present device, a user disengages each of the lips from the recess to open the cover. The user exfoliates his feet by rubbing each foot back and forth across a top one of the sand paper sheets. The trough catches the shavings from each foot. The mirror allows a user to inspect his feet to determine whether exfoliation is complete. The construction of the device permits a user to exfoliate his feet from a relaxed seated position.

Thus has been broadly outlined the more important features of the present foot exfoliation device so that the detailed description thereof that follows may be better understood and in order that the present contribution to the art may be better appreciated.

BRIEF DESCRIPTION OF THE DRAWINGS

Figures

DETAILED DESCRIPTION OF THE DRAWINGS

Figure 1:
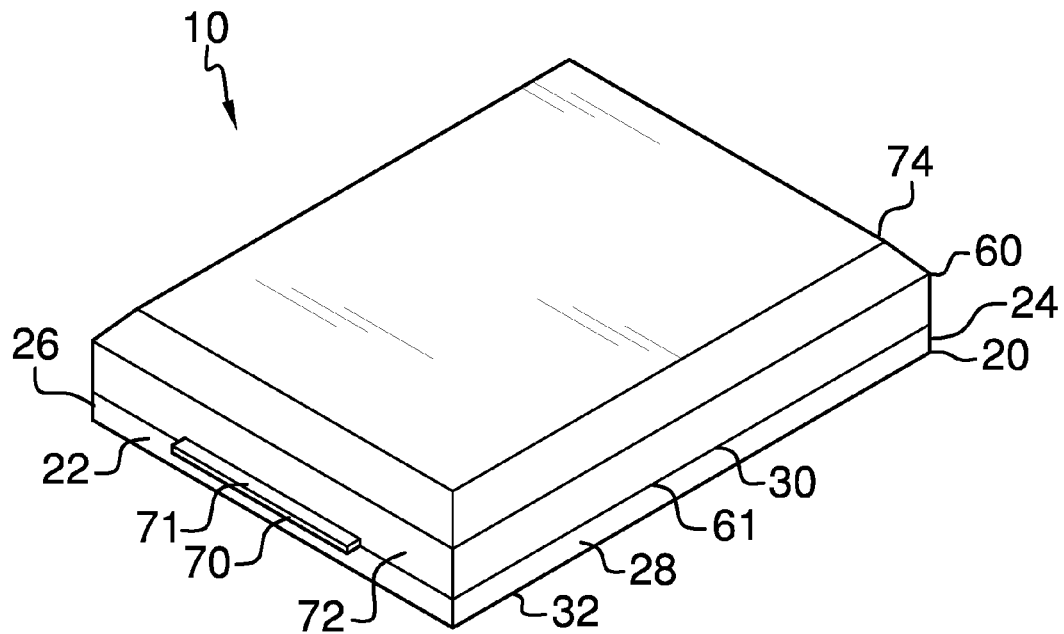
FIG. 1 is an isometric view in a closed position.
Figure 2:
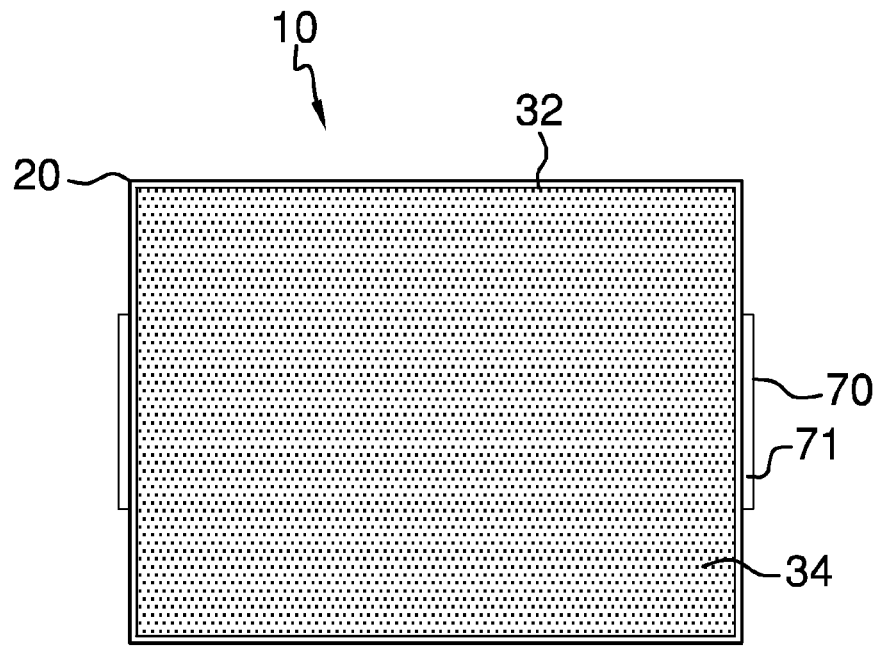
FIG. 2 is a bottom plan view.
Figure 3:
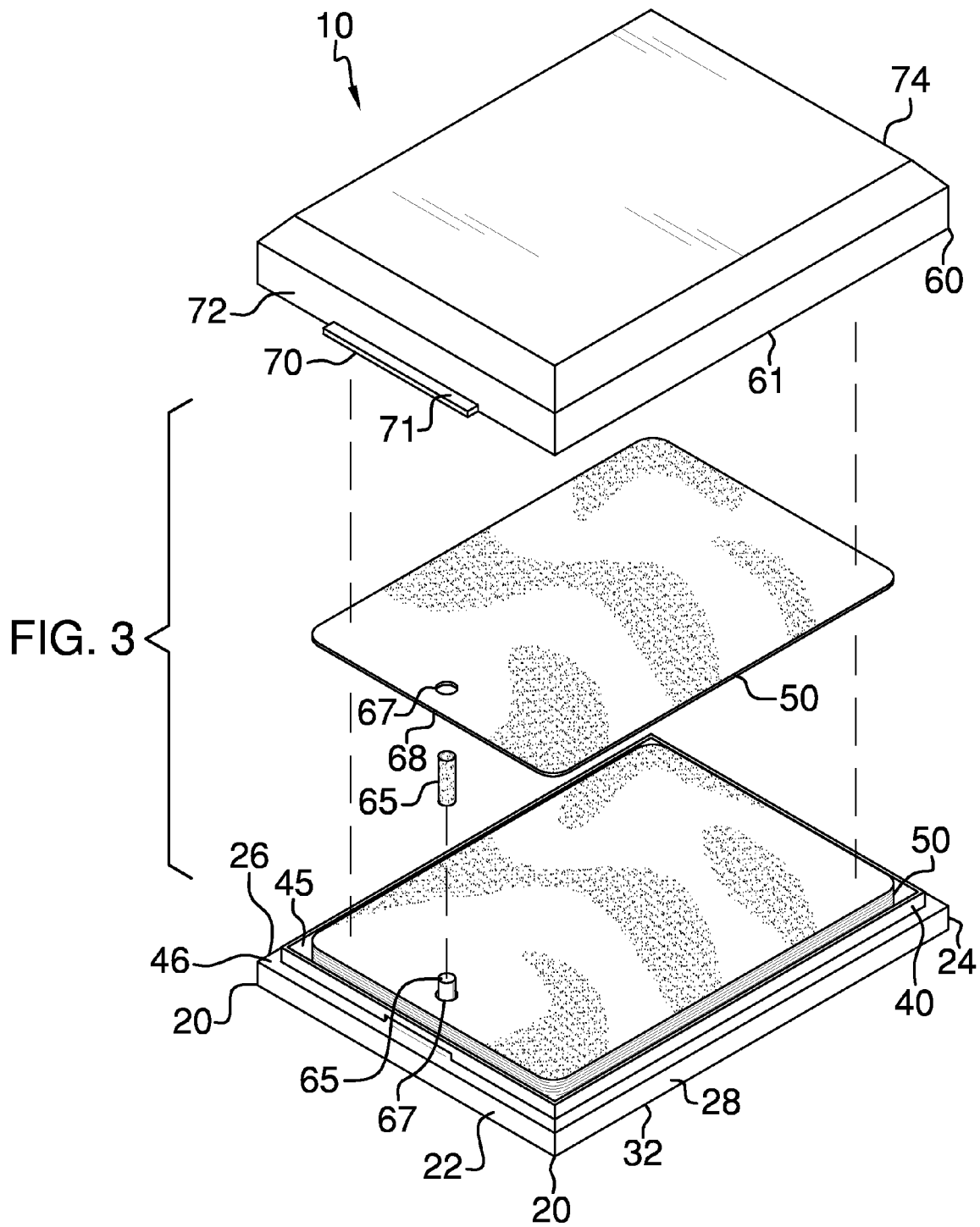
FIG. 3 is an exploded isometric view.
Figure 4:
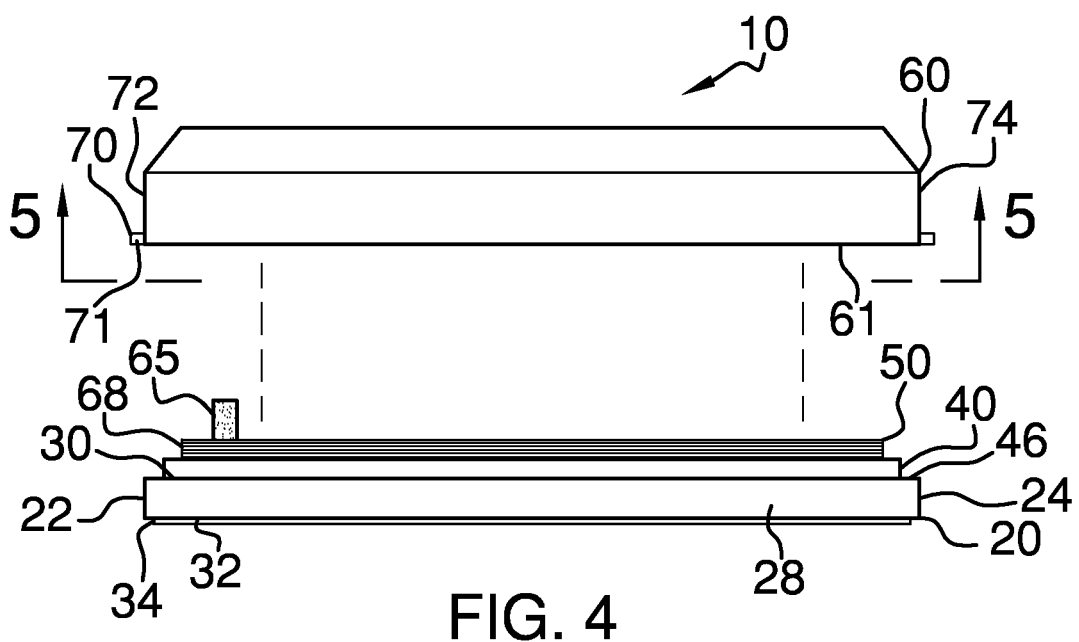
FIG. 4 is an exploded side elevation view.
Figure 5:
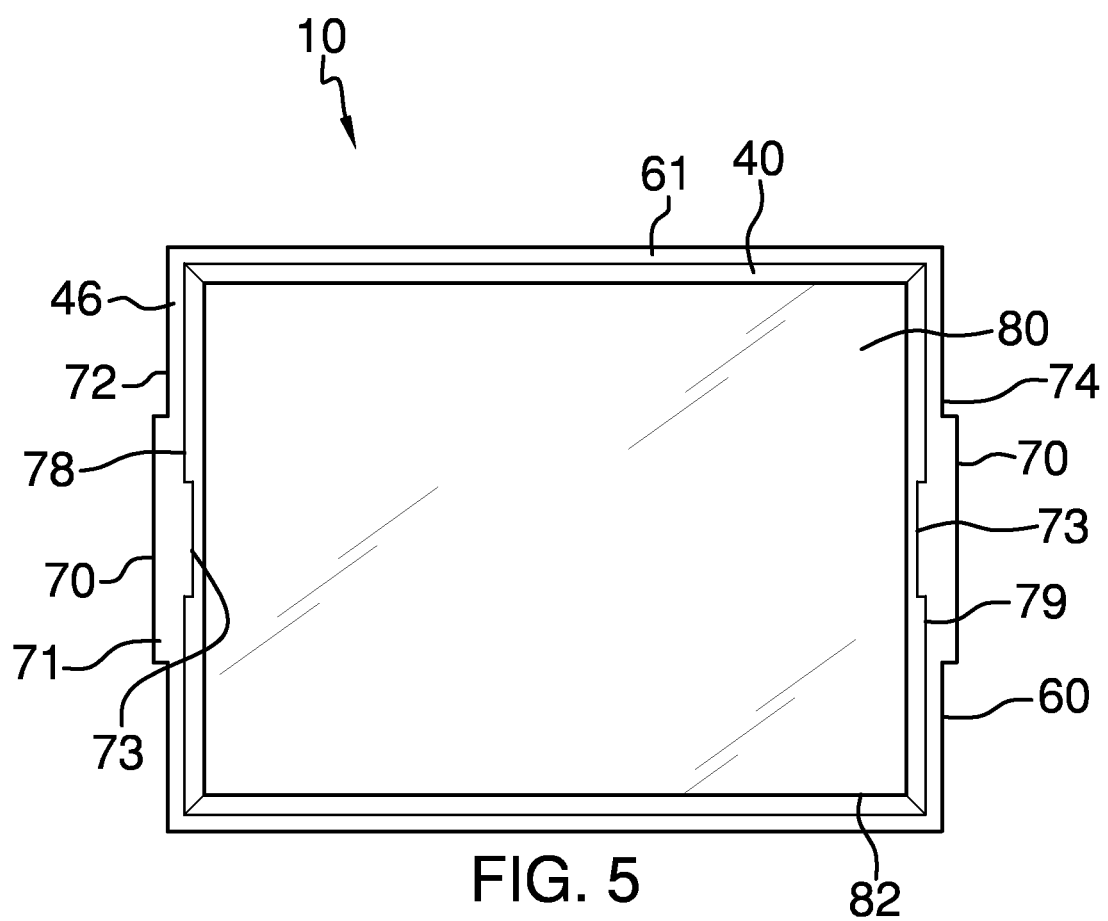
FIG. 5 is a bottom plan view of the cover.
Figure 6:
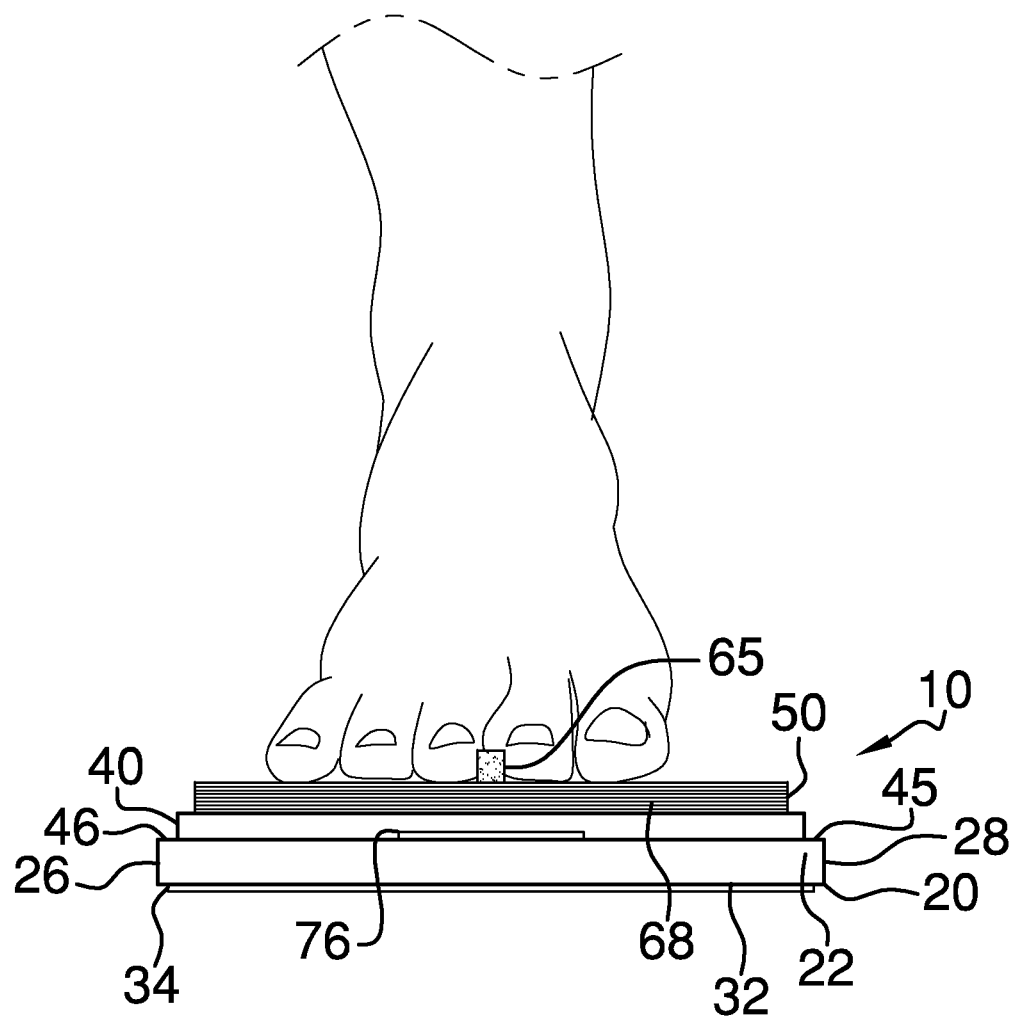
FIG. 6 is an in-use front elevational view.

With reference now to the drawings, and in particular FIGS. 1 through 6 thereof, example of the instant foot exfoliation device employing the principles and concepts of the present foot exfoliation device and generally designated by the reference number 10 will be described.

Referring to FIGS. 1 through 6 a preferred embodiment of the present foot exfoliation device 10 is illustrated. The foot exfoliation device 10 is portable and lightweight. The present device 10 includes a base tray 20. The base tray 20 has a front end 22, a rear end 24, a left end 26, a right end 28, a top side 30, and a bottom side 32. A non-slip surface member 34 is disposed on the bottom side 32 of the base tray 20 to prevent the device 10 from moving during use to exfoliate a user's feet.

A continuous wall 40 is disposed on the base tray 20 top side 30 proximal the periphery thereof. A trough 45 is disposed within the base tray 20 inside the wall 40. The trough 45 covers substantially the entire top side 30 of the base tray 20. A ledge 46 is continuously disposed on the base tray 20 top side 30 outside the wall 40.

A plurality of sand paper sheets 50 is disposed within the trough. The sand paper sheets 50 are stacked atop each other. The trough 45 covers substantially the entire top side 30 of the base tray 20 to permit the containment of larger sand paper sheets and, thus, a larger exfoliation surface area than a smaller trough would permit. A removable cover 60 is disposed atop the base tray 20.

The instant foot exfoliation device 10 also includes a sand paper post member 65 centrally disposed within the trough 45 proximal to the front end 22 of the base tray 20. An aperture 67 is centrally disposed proximal to a forward end 68 of each of the sand paper sheets 50. Each aperture 67 slidingly receives the post member 65 therethrough to secure the sand paper sheets 50 within the trough 45.

A lip 70 having a forward extension member 71 and a rearward extension member 73 is centrally disposed on at least one of a front side 72 and a rear side 74 of the cover 60. A recess 76 is centrally disposed on at least one of a forward side 78 and a rearward side 79 of the wall 40. The lip 70 rearward extension member 73 lockingly engages and alternately disengages the recess 76. Upon the locking engagement of the lip 70 rearward extension member 73 with the recess 76, the cover 60 is placed in a closed position. Alternately upon the disengagement of the lip 70 rearward extension member 73 from the recess 76, the cover 60 is placed in an open position. The cover 60, thus, snaps onto the base tray 20 with an outside perimeter 61 of the cover 60 disposed atop the ledge 46 of the base tray 20 when the cover 60 is in a closed position. The forward extension member 71 provides a grip for removing the cover 60 from the base tray 20.

In addition, a mirror 80 is disposed on an underside 82 of the cover 60. The mirror 80 is disposed on the entire surface of the cover 60 underside 82. The mirror 80 is unbreakable.

To use the present device 10, a user disengages each lip 70 from the recess 76 to open the cover 60. The user exfoliates his feet by rubbing each foot back and forth across a top one of the sand paper sheets 50. The trough 45 catches the shavings from each foot. The mirror 80 allows a user to inspect his feet to determine whether the exfoliation is complete without placing the user's body in a contorted position in order to inspect his feet. The construction of the device 10 permits a user to exfoliate his feet while sitting in a relaxed position. The sand paper post member 65 permits exfoliation between the user's toes.

What is claimed is:

1. A foot exfoliation device comprising:
   a base tray having a front end, a rear end, a left end, a right end, a top side, and a bottom side;
   a continuous wall disposed on the base tray top side proximal the periphery thereof;
   a trough disposed within the base tray inside the wall, the trough substantially covering the entire top side of the base tray;
   a plurality of sand paper sheets disposed within the trough, the sand paper sheets stacked atop each other;
   a removable cover disposed atop the base tray; and
   a sand paper post member centrally disposed within the trough and proximal to the front end of the base tray.

2. The foot exfoliation device of claim 1 further comprising:
   an aperture centrally disposed proximal to a forward end of each of the sand paper sheets;
   wherein each aperture slidingly receives the post member therethrough.

3. The foot exfoliation device of claim 2 further comprising:
   a lip centrally disposed on at least one of a front side and a rear side of the cover, the lip having a forward extension member and a rearward extension member;
   a recess centrally disposed on at least one of a forward side and a rearward side of the wall;
   a ledge continuously disposed on the base tray top side outside the wall;
   wherein the lip rearward extension member lockingly engages and alternately disengages the recess;
   wherein upon the locking engagement of the lip rearward extension member with the recess, the cover is placed in a closed position with an outside perimeter of the cover disposed atop the ledge of the base tray and alternately upon the disengagement of the lip rearward extension member from the recess, the cover is placed in an open position.

4. The foot exfoliation device of claim 3 further comprising a mirror disposed on an underside of the cover.

5. The foot exfoliation device of claim 4 wherein the mirror is disposed on the entire surface of the cover underside.

6. The foot exfoliation device of claim 5 further comprising a non-slip surface member disposed on the bottom side of the base tray.

\* \* \* \* \*